(12) United States Patent
Koivisto et al.

(10) Patent No.: US 10,517,510 B2
(45) Date of Patent: Dec. 31, 2019

(54) METHOD AND APPARATUS FOR PRODUCING INFORMATION INDICATIVE OF CARDIAC MALFUNCTIONS

(71) Applicant: PRECORDIOR OY, Turku (FI)

(72) Inventors: Tero Koivisto, Turku (FI); Tuomas Valtonen, Turku (FI); Mikko Pankaala, Raisio (FI); Tero Hurnanen, Pernio (FI); Tom Kuusela, Turku (FI)

(73) Assignee: PRECORDIOR OY, Turku (FI)

( * ) Notice: Subject to any disclaimer, the term of this patent is extended or adjusted under 35 U.S.C. 154(b) by 330 days.

(21) Appl. No.: 15/554,644

(22) PCT Filed: Feb. 26, 2016

(86) PCT No.: PCT/FI2016/050121
§ 371 (c)(1),
(2) Date: Aug. 30, 2017

(87) PCT Pub. No.: WO2016/142575
PCT Pub. Date: Sep. 15, 2016

(65) Prior Publication Data
US 2018/0035919 A1    Feb. 8, 2018

(30) Foreign Application Priority Data

Mar. 11, 2015 (FI) .................................. 20155160

(51) Int. Cl.
*A61B 5/11* (2006.01)
*A61B 5/00* (2006.01)
(Continued)

(52) U.S. Cl.
CPC .......... *A61B 5/1102* (2013.01); *A61B 5/0004* (2013.01); *A61B 5/02405* (2013.01);
(Continued)

(58) Field of Classification Search
CPC . A61B 5/1102; A61B 5/0004; A61B 5/02405; A61B 5/046; A61B 5/7246;
(Continued)

(56) References Cited

U.S. PATENT DOCUMENTS 5,365,426 A    11/1994 Siegel et al.
6,024,705 A    2/2000 Schlager et al.
(Continued)

FOREIGN PATENT DOCUMENTS

WO    2010/067294 A1    6/2010
WO    2010/145009 A1    12/2010
(Continued)

OTHER PUBLICATIONS

Wu et al., "Research on the Method of Characteristic Extraction and Classification of Phonocardiogram", 2012 International Conference on Systems and Informatics (ICSAI 2012), May 19, 2012, pp. 1732-1735.

(Continued)

*Primary Examiner* — Lindsey G Wehrheim
(74) *Attorney, Agent, or Firm* — Young & Thompson

(57) ABSTRACT

An apparatus for producing information indicative of cardiac malfunctions, for example atrial fibrillation, includes a processing system for processing an analysis signal produced by a sensor system responsive to motion including cardiovascular motion. The processing system is configured to form a first indicator quantity indicating degree of concentration of the autocorrelation of the analysis signal to a point corresponding to zero time difference between analysis signal samples whose mutual correlation is expressed by the autocorrelation and a second indicator quantity indicating the spectral entropy of the analysis signal. The processing system is configured to determine an indicator of cardiac (Continued)

malfunction on the basis of at least the first indicator quantity and the second indicator quantity.

17 Claims, 4 Drawing Sheets

(51) Int. Cl.
*A61B 5/024* (2006.01)
*A61B 5/046* (2006.01)

(52) U.S. Cl.
CPC ............ *A61B 5/046* (2013.01); *A61B 5/7246* (2013.01); *A61B 5/7257* (2013.01); *A61B 5/7267* (2013.01); *A61B 5/7282* (2013.01); *A61B 2562/0219* (2013.01)

(58) Field of Classification Search
CPC ... A61B 5/7257; A61B 5/7267; A61B 5/7282; A61B 2562/0219
See application file for complete search history.

(56) References Cited

U.S. PATENT DOCUMENTS

| | | | |
|---|---|---|---|
| 2008/0194975 | A1 | 8/2008 | MacQuarrie et al. |
| 2009/0275849 | A1 | 11/2009 | Stewart |
| 2013/0324812 | A1 | 12/2013 | Brainard, II et al. |

FOREIGN PATENT DOCUMENTS

| | | |
|---|---|---|
| WO | 2012/149652 A1 | 11/2012 |
| WO | 2013/160538 A1 | 10/2013 |

OTHER PUBLICATIONS

Hernandez et al., "BioGlass: Physiological Parameter Estimation Using a Head-mounted Wearable Device", 4th International Conference on Wireless Mobile Communication and Healthcare, Jan. 1, 2014, pp. 55-58.

Morbiducci et al., "Optical Vibrocardiography: A Novel Tool for the Optical Monitoring of Cardiac Activity", Annals of Biomedical Engineering, Nov. 3, 2006, pp. 45-58, vol. 35, No. 1.

Kamath, "Quantification of Electrocardiogram Rhythmicity to Detect Life Threatening Cardiac Arrhythmias Using Spectral Entropy", Journal of Engineering Science and Technology, Oct. 2013, pp. 588-602, vol. 8, No. 5.

Brown et al., "A new technique for the identification of respiratory sinus arrhythmia in utero", Journal of Biomedical Engineering, May 1992, pp. 263-267, vol. 14, No. 3.

Nagae et al., "Measurement of heart rate variability and stress evaluation by using microwave reflectometric vital signal sensing", Review of Scientific Instruments, Sep. 13, 2010, vol. 81, No. 9.

Suinesiaputra et al., "Automated Detection of Regional Wall Motion Abnormalities Based on a Statistical Model Applied to Multislice Short-Axis Cardiac MR Images", IEEE Transactions on Medical Imaging, Apr. 2009, pp. 595-607, vol. 28, No. 4.

Abasolo et al., "Entropy analysis of the EEG background activity in Alzheimer's disease patients", Physiological Measurement, 2006, pp. 241-253, vol. 27, No. 3.

International Search Report, dated May 18, 2016, from corresponding PCT application No. PCT/FI2016/050121.

FI Search Report, dated Nov. 9, 2015, from corresponding FI application No. 20155160.

$\tau = 0$ $\tau = 0$

METHOD AND APPARATUS FOR PRODUCING INFORMATION INDICATIVE OF CARDIAC MALFUNCTIONS

FIELD OF THE DISCLOSURE

The disclosure relates generally to producing information indicative of cardiac malfunctions, such as for example atrial fibrillation. More particularly, the disclosure relates to an apparatus and to a method for producing information indicative of cardiac malfunctions. Furthermore, the disclosure relates to a computer program for producing information indicative of cardiac malfunctions.

BACKGROUND

Malfunctions and abnormalities that may occur in the cardiovascular system, if not diagnosed and appropriately treated or remedied, may progressively decrease the ability of the cardiovascular system to supply, inter alia, sufficient oxygen to satisfy the coronary oxygen demand when the individual encounters stress. Currently, methods such as cardiography based on electromagnetic phenomena related to cardiac activity, echocardiography, and cardiography based on cardiovascular motion are used in the identification and assessment of various cardiac malfunctions and abnormalities. A well-known example of the cardiography based on electromagnetic phenomena related to cardiac activity is the electrocardiography "ECG", and examples of the cardiography based on cardiovascular motion are ballistocardiography "BCG" and seismocardiography "SCG". The echocardiography provides images of sections of the heart and can provide comprehensive information about the structure and function of the heart, but requires expensive equipment and specialised operating personnel. The ECG provides a fairly rapid electrical assessment of the heart, but does not provide any information relating to forces of contraction. The cardiography based on cardiovascular motion involves measurement of a signal indicative of cardiovascular motion. Earlier, the signal was obtained while an individual lay on a bed that was provided with an apparatus for measuring movements or there was a facilitating apparatus that was attached across the shin area of the legs. Currently, the signal can be obtained using small sensor elements, e.g. accelerometers, which are suitable for measuring minute movements which are representative of movements of the heart. A sensor used in cardiography based on cardiovascular motion can be as well a gyroscope configured to obtain a signal indicative of rotational movement of a chest of an individual. Signal processing means are configured to generate, from the signal, indicator data that is indicative of cardiac operation of the individual. The operation of a gyroscope is not affected by gravity. Thus, the measurement is practically independent of the position or posture of the monitored individual. It has been noted that the external angular motion of the chest is orders of magnitude larger than what one could anticipate from the mere extent of the heart rotation and the ratio between the size of the heart and the diameter of the human chest. It has also been noted that the detection of the angular motion is also relatively insensitive to the location of the sensor with respect to the heart. Thus, relatively accurate measurements can be made with even one gyroscope, for example microelectromechanical gyroscope, attached to the chest of the individual under consideration. Microelectromechanical gyroscopes are accurate, small in size and commercially available.

FIGS. 1a and 1b show the relationship between rhythmic electrical functions and related cardiovascular motions. FIG. 1a shows an example of an ECG waveform and FIG. 1b shows a waveform of an exemplifying signal indicative of cardiovascular motion and measured with an accelerometer in the "head-to-foot"-direction that is typically referred to as the y-direction. For the sake of illustrative purposes, a brief explanation of basic heart functions is provided below.

The heart includes four chambers. The right atrium is interconnected with the right ventricle by the tricuspid valve, and the left atrium is interconnected with the left ventricle by the mitral valve. Blood is delivered to the right atrium from the upper half of the body via the superior vena cava, and from the lower half of the body via the inferior vena cava. The tricuspid valve is opened by concurrent contraction of the right atrium myocardium and the right ventricular papillary muscles thereby allowing blood flow from the right atrium into the right ventricle. Then the tricuspid valve closes when the papillary muscles relax. When the myocardium of the right ventricle contracts, blood is forced from the right ventricle through the pulmonary valve into the pulmonary artery which delivers the blood into the lungs wherein it is oxygenated. The oxygenated blood is then delivered to the left atrium via pulmonary veins. The oxygenated blood flows from the left atrium into the left ventricle when the mitral valve is opened by concurrent contraction of the left atrium myocardium and the left ventricular papillary muscles thereby allowing blood flow from the left atrium into the left ventricle. Then the mitral valve is closed when the papillary muscles relax. The oxygenated blood is then forced out from the left ventricle through the aortic valve into the aorta which delivers the oxygenated blood to the peripheral vascular system.

Each heart-beat period involves three major stages: the atrial systole, the ventricular systole and the cardiac diastole. The atrial systole is the period of contraction of the heart muscles encompassing the right and left atria. Both atria contract concurrently with the papillary muscle contraction thereby forcing open the tricuspid valve and the mitral valve. The electrical activity, i.e. the electrical systole, which stimulates the muscle tissue of the chambers of the heart to make them contract begins in the sinoatrial node located in the right atrium. The conduction electrical depolarization continues to travel as a wave downwards, leftwards, and posteriorly through both atria depolarising each atrial muscle cell in turn. This propagation of charge can be seen as the P-wave on the ECG waveform shown in FIG. 1a. This is closely followed by mechanical contraction of the atria that is detected as an impact which corresponds to the h-peak of the waveform shown in FIG. 1b and to the recoil which corresponds to the i-valley of the waveform shown in FIG. 1b. When the right and left atria begin to contract, there is a high velocity flow of blood into the right and left ventricles, which is represented by the j-peak on the waveform shown in FIG. 1b. The continuing atrial contraction, when the tricuspid valve begins to close, causes an additional lower velocity flow of blood into the right and left ventricles. The additional flow of blood is called the "atrial kick", which corresponds to the "a-a$^1$"-wave complex in the waveform shown in FIG. 1b. After the atria are emptied, the tricuspid and mitral valves close thereby giving rise to the downward g-wave on the waveform shown in FIG. 1b. The ventricular systole is the contraction of the muscles of the left and right ventricles, and is caused by the electrical depolarization of the ventricular myocardia giving rise to the "Q-R-S"-wave complex in the ECG waveform shown in FIG. 1a. The downward Q-wave is caused by the downward flow of depolarisation through the septum along a specialized group of cells called "the bundle of His". The R-peak is caused by depolarization of the ventricular muscle tissue, and the S-wave is produced by depolarization of the heart tissue between the atria and ventricles. As the depolarization travels down the septum and throughout the ventricular myocardia, the atria and sinoatrial node start to polarise. The closing of the tricuspid and mitral valves mark the beginning of ventricular systole and cause the first part of the "lub-dub" sound made by the heart as it beats. This sound is typically known as the "first heart tone". When the electrical depolarization of the ventricular myocardia peaks, the atrioventricular "AV" septum separating the right and left ventricles contracts causing an impact, which corresponds to the H-peak on the waveform shown in FIG. 1b, and a recoil which corresponds to the I-valley on the waveform shown in FIG. 1b. The ventricular contraction forces the blood from the right ventricle into the pulmonary artery through the pulmonary valve, and from the left ventricle into the aorta through the aortic valve under very high velocity thereby causing the J-peak on the waveform shown in FIG. 1b. The deceleration of blood flow from the left ventricle into the aorta causes the downward K-wave on the waveform shown in FIG. 1b. When the left ventricle empties, its pressure falls below the pressure in the aorta and the aortic valve closes. Similarly, when the pressure in the right ventricle falls below the pressure in the pulmonary artery, the pulmonary valve closes. The second part of the "lub-dub" sound, which is typically known as the "second heart tone", is caused by the closure of the pulmonary and aortic valves at the end of ventricular systole thereby causing the upward L-wave on the waveform shown in FIG. 1b. Concurrently with the closing of the pulmonary and aortic valves, the atrioventricular "AV" septum relaxes and moves upward and the ventricular myocardia is re-polarized giving rise to the T-wave on the ECG waveform shown in FIG. 1a. The cardiac diastole, which includes the atrial diastole and the ventricular diastole, is the period when the heart relaxes after contraction and prepares for being refilled with circulating blood. Atrial diastole is when the right and left atria are relaxing, and the ventricular diastole is when the right and left ventricles are relaxing. During the period of the atrial diastole, the right atrium is re-filled by deoxygenated blood while the left atrium is re-filled with oxygenated blood. Re-filling of the atria causes the downward M-wave on the waveform shown in FIG. 1b early in the diastole which coincides with repolarization of the bundle of His cells, which is shown as the U-wave in the ECG waveform. When the right and left atria are filled to their maximum capacities, the reflux of blood against the tricuspid valve and mitral valve cause the upward N-wave on the waveform shown in FIG. 1b.

Publication WO2012149652 describes a method for assessment of cardiac contractility in a subject by recording precordial acceleration signals.

Publication US2008194975 describes a method for monitoring an individual's physiological condition and detecting abnormalities therein. The method comprises concurrently receiving a first signal that is an ECG signal and a second signal indicative of cardiovascular motion.

Analysis of waveforms indicative of cardiovascular motion is typically performed visually by qualified diagnosticians in order to distinguish abnormal cardiovascular function from normal cases. In many cases, however, it may be challenging to find out certain cardiac malfunctions, such as for example atrial fibrillation, by visual analysis. Thus, a need exists for methods and apparatuses for producing information indicative of cardiac malfunctions.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new method for producing information indicative of cardiac malfunctions, e.g. atrial fibrillation. A method according to the invention comprises:

forming a first indicator quantity indicating degree of concentration of the autocorrelation of an analysis signal to a point that corresponds to zero time difference between analysis signal samples whose mutual correlation is expressed by the autocorrelation, forming a second indicator quantity indicating the spectral entropy of the analysis signal, and determining an indicator of cardiac malfunction on the basis of at least the first indicator quantity and the second indicator quantity.

The above-mentioned analysis signal is a signal produced by a sensor system responsive to motion including cardiovascular motion. The sensor system may comprise for example an accelerometer, a gyroscope, and/or an inertial measurement unit "IMU" comprising both an accelerometer and a gyroscope.

The autocorrelation, as a general concept, has the property that, when irregularity of the waveform of a signal under consideration increases, the autocorrelation gets more and more concentrated to a point that corresponds to zero time difference between signal samples whose mutual correlation is expressed by the autocorrelation. The autocorrelation R of the above-mentioned analysis signal can be defined for example as:

$$R(\tau)=E\{(S(t)-\mu)\times(S(t-\tau)-\mu)\}/\sigma^2, \qquad (1)$$

where E is the expected value operator, S is the analysis signal, t is time, $\tau$ is the time difference between analysis signal samples whose mutual correlation is expressed by the autocorrelation, $\mu$ is the average, i.e. the arithmetic average, of the analysis signal, and $\sigma^2$ is the variance of the analysis signal. For example, if the analysis signal were totally non-periodical such as ideal white noise "IWN" which has extremely irregular waveform, there would be zero correlation between any analysis signal samples separated by a non-zero time difference, and thus the autocorrelation $R(\tau)$ of the analysis signal would be only a single peak at the point $\tau=0$.

Forming the above-mentioned first indicator quantity indicating the degree of concentration of the autocorrelation can be based on computing an estimate of the autocorrelation of the analysis signal or an estimate of the frequency spectrum of the analysis signal. The frequency spectrum is closely related to the autocorrelation because the power spectral density "PSD" is the Fourier transformation of the autocorrelation and PSD~F(f)×F*(f), where F(f) and F*(f) are the frequency spectrum and its complex conjugate. The frequency spectrum, as a general concept, has the property that, when irregularity of the waveform of a signal under consideration increases, the frequency spectrum gets more and more evenly distributed. For example, if the analysis signal were totally non-periodical such as ideal white noise, the frequency spectrum of the analysis signal would be totally flat. This property of the frequency spectrum can be used for obtaining the first indicator quantity indicating the degree of concentration of the autocorrelation.

The spectral entropy, as a general concept, has the property that the spectral entropy increases when irregularity of the waveform of a signal under consideration increases and thereby the power spectral density of the signal under consideration gets more flat. Thus, the spectral entropy is indicative of the degree of flatness of the power spectral density of the signal under consideration. The spectral entropy SE of the above-mentioned analysis signal can be defined for example as:

$$SE = -\int_B \{PSD_n(f)\log_2[PSD_n(f)]\}df \quad (2)$$

where f is the frequency, $PSD_n(f)$ is the normalized power spectral density being the power spectral density of the analysis signal divided by the power of the analysis signal, and B is the frequency band of the analysis signal. For example, if the analysis signal were a pure sinusoid, the normalized power spectral density would have peaks having the height $2^{-1}$ at f=frequency of the sinusoid and at f=−frequency of the sinusoid. In this exemplifying case, the above-defined spectral entropy SE is 1. For another example, if the analysis signal were totally non-periodical such as ideal white noise, the power spectral density of the analysis signal would be totally flat. In this case, we can assume that there $2^N$ frequency points in the discrete Fourier transformation, e.g. the Fast Fourier Transform "FFT", where N is an integer. In this exemplifying case, the normalized power spectral density has a value $2^{-N}$ at each of the $2^N$ frequency points, and the above-defined spectral entropy SE is N.

Cardiac malfunctions, e.g. atrial fibrillation, which may be sometimes challenging to diagnose, may however cause irregularities on the waveform of the above-mentioned analysis signal. These irregularities may be difficult to detect from waveforms of one or two heart-beat periods but they manifest themselves in longer time periods covering several successive heart-beat periods so that the autocorrelation is more concentrated on the point that corresponds to zero time difference than normally and so that the spectral entropy has a higher value than normally. Therefore, the above-mentioned first and second indicator quantities that indicate the degree of irregularity of the analysis signal represent information indicative of cardiac malfunctions, e.g. atrial fibrillation.

In accordance with the invention, there is provided also a new apparatus for producing information indicative of cardiac malfunctions. The apparatus according to the invention comprises a processing system for processing an analysis signal produced by a sensor system responsive to motion including cardiovascular motion. The processing system is configured to:

form a first indicator quantity indicating degree of concentration of the autocorrelation of the analysis signal to a point that corresponds to zero time difference between analysis signal samples whose mutual correlation is expressed by the autocorrelation, form a second indicator quantity indicating the spectral entropy of the analysis signal, and determine an indicator of cardiac malfunction on the basis of at least the first indicator quantity and the second indicator quantity.

The apparatus may further comprise the above-mentioned sensor system for producing the analysis signal. It is, however, emphasized that the apparatus does not necessarily comprise any sensor system but the apparatus may comprise a signal interface for connecting to an external sensor system. A sensor element comprising the sensor system may further comprise a processor for detecting whether an individual measured with the sensor system is at rest and for extracting the analysis signal from an output signal of the sensor system so that the analysis signal corresponds to a situation where the individual is at rest. It is also possible that the processing system configured to determine the indicator of cardiac malfunction is also configured to detect, from the output signal of the sensor system, periods when the individual is at rest and to extract the analysis signal from the output signal of the sensor system so that the analysis signal corresponds to a situation where the individual is at rest.

In accordance with the invention, there is provided also a new computer program for producing information indicative of cardiac malfunctions on the basis of the above-mentioned analysis signal. The computer program comprises computer executable instructions for controlling a programmable processing system to:

form a first indicator quantity indicating degree of concentration of the autocorrelation of the analysis signal to a point that corresponds to zero time difference between analysis signal samples whose mutual correlation is expressed by the autocorrelation, form a second indicator quantity indicating the spectral entropy of the analysis signal, and determine an indicator of cardiac malfunction on the basis of at least the first indicator quantity and the second indicator quantity.

In accordance with the invention, there is provided also a new computer program product. The computer program product comprises a non-volatile computer readable medium, e.g. a compact disc "CD", encoded with a computer program according to the invention.

A number of exemplifying and non-limiting embodiments of the invention are described in accompanied dependent claims.

Various exemplifying and non-limiting embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of also un-recited features. The features recited in the accompanied dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

Exemplifying and non-limiting embodiments of the invention and their advantages are explained in greater detail below with reference to the accompanying drawings, in which:

FIGS. 1a and 1b have already been explained when describing the background of the invention.

DESCRIPTION OF EXEMPLIFYING AND NON-LIMITING EMBODIMENTS

The specific examples provided in the description below should not be construed as limiting the scope and/or the applicability of the appended claims. Lists and groups of examples provided in the description are not exhaustive unless otherwise explicitly stated.

Figure 1A:
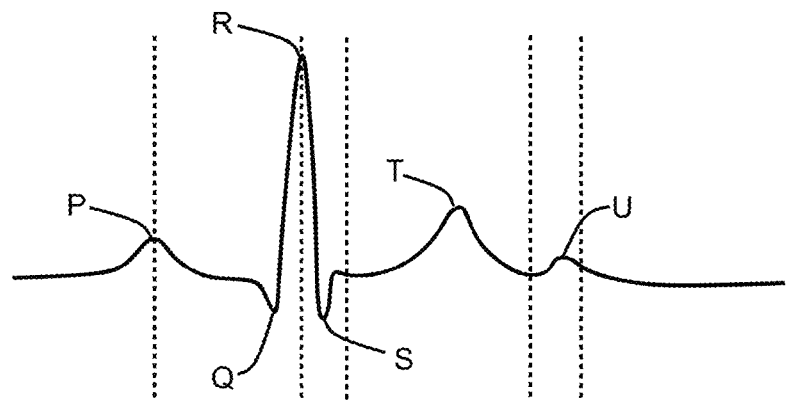
FIG. 1a shows an example of an electrocardiography "ECG" waveform and FIG. 1b shows a waveform of an exemplifying signal indicative of cardiovascular motion.
Figure 1B:
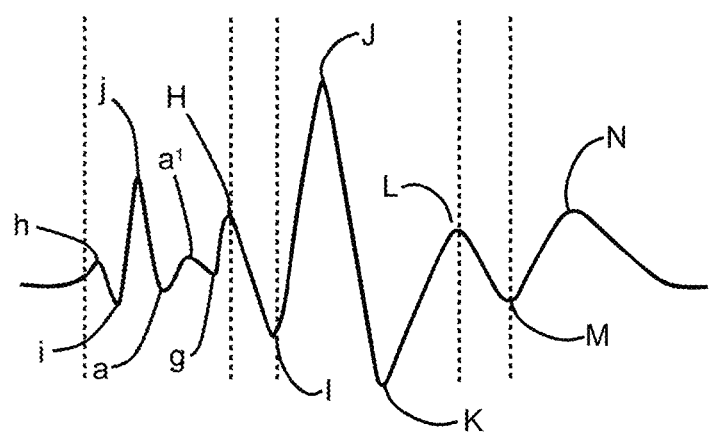
Figure 2:
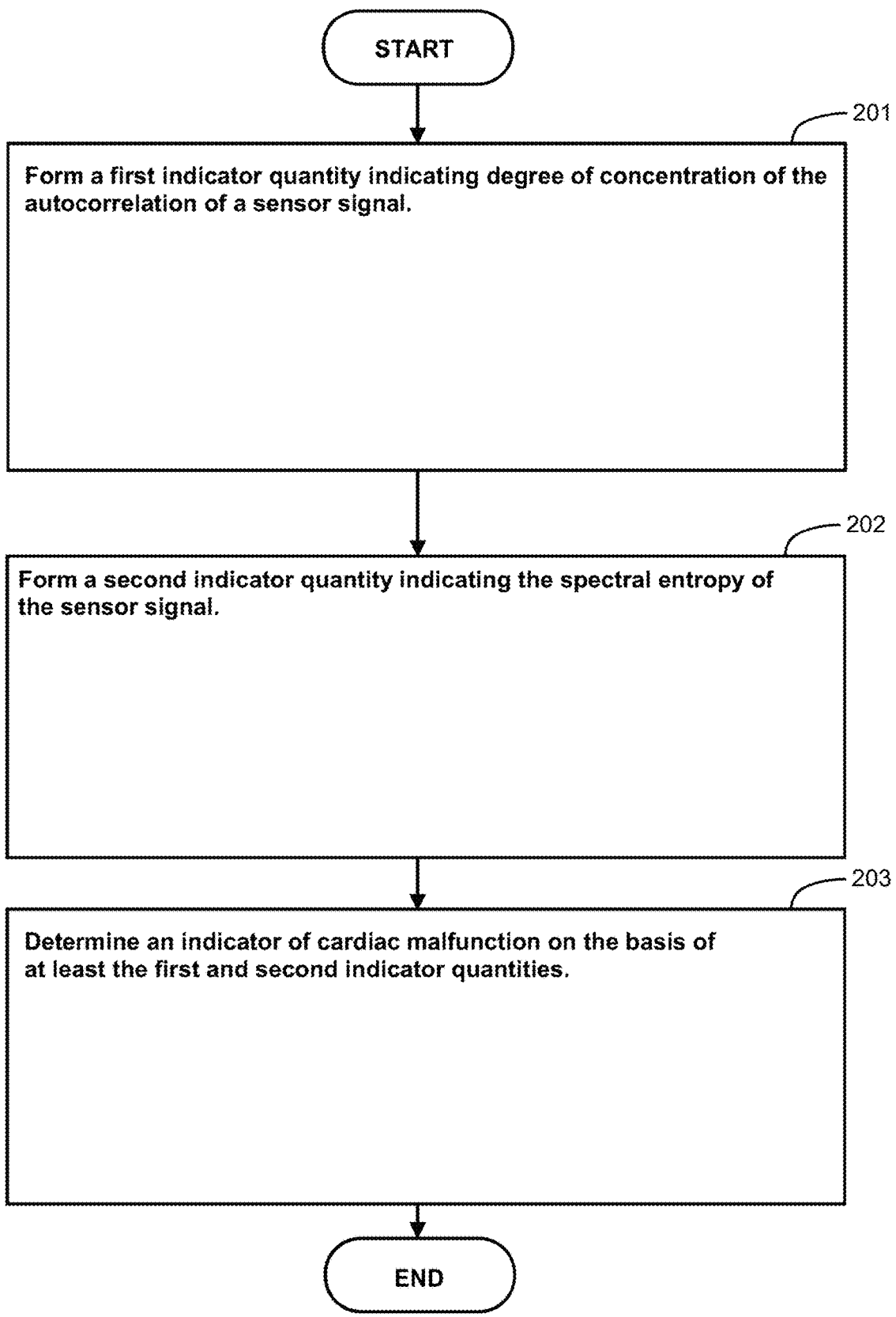
FIG. 2 shows a flowchart of a method according to an exemplifying and non-limiting embodiment of the invention for producing information indicative of cardiac malfunctions.

FIG. 2 shows a flowchart of a method according to an exemplifying and non-limiting embodiment of the invention for producing information indicative of cardiac malfunctions, e.g. atrial fibrillation. The method comprises the following actions:
action 201: forming a first indicator quantity indicating degree of concentration of the autocorrelation of an analysis signal to a point that corresponds to the zero time difference between analysis signal samples whose mutual correlation is expressed by the autocorrelation,
action 202: forming a second indicator quantity indicating the spectral entropy of the analysis signal, and
action 203: determining an indicator of cardiac malfunction on the basis of at least the first indicator quantity and the second indicator quantity.

The above-mentioned analysis signal is a signal produced by a sensor system that is responsive to motion including cardiovascular motion. The analysis signal corresponds advantageously to a situation where an individual under consideration is at rest. The sensor system may comprise for example an accelerometer, a gyroscope, and/or an inertial measurement unit "IMU" comprising both an accelerometer and a gyroscope. The sensor system can be for example a microelectromechanical system "MEMS". The temporal duration of the analysis signal can be, for example but not necessarily, from five to ten seconds.

A method according to an exemplifying and non-limiting embodiment of the invention comprises detecting, from an output signal of the sensor system, a period when the individual is at rest and extracting the analysis signal from the output signal of the sensor system so that the analysis signal corresponds to a situation where the individual is at rest.

Cardiac malfunction, e.g. atrial fibrillation, can be deemed to be present when the above-mentioned first indicator quantity exceeds a first threshold value and the above-mentioned second indicator quantity exceeds a second threshold value. The first and second threshold values can be determined on the basis of empirical data gathered from a group of patients and/or other persons. The first and second threshold values are not necessary constants but one or both of these threshold values can be changing according to the individual under consideration, according to time, and/or according to some other factors. It is also possible to construct a series of threshold value pairs each constituted by one first threshold value and one second threshold value so that each threshold value pair represents a specific probability of atrial fibrillation or some other cardiac malfunction and/or abnormality.

In order to improve the reliability, the first and second indicator quantities can be determined for each of two or more analysis signals that are mutually different temporal portions of the output signal of the sensor system and that are measured advantageously when the individual is at rest. The indicator of cardiac malfunction can be determined on the basis the first and second indicator quantities determined for the two or more analysis signals.

In order to further improve the reliability, different ones of the above-mentioned two or more analysis signals can be received from different measuring means of the sensor system. For example, one or more of the analysis signals can be received from an accelerometer and one or more others of the analysis signals can be received from a gyroscope.

Figure 3A:
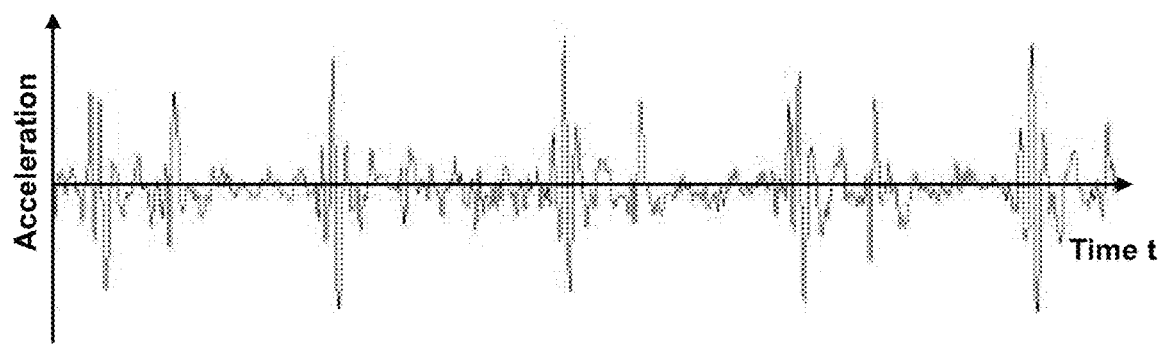
FIG. 3a shows a waveform of an exemplifying analysis signal measured with a sensor system responsive to motion in a normal case when an individual under consideration is at rest.
Figure 4A:
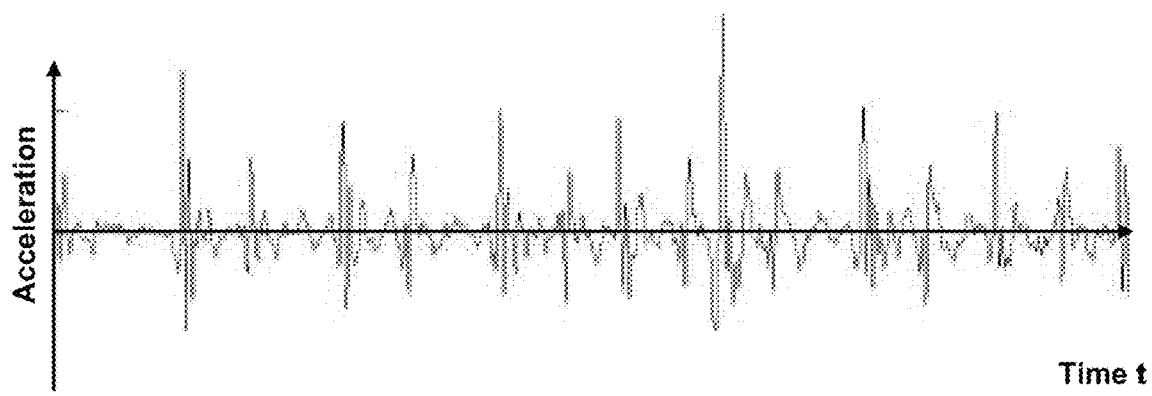
FIG. 4b shows the autocorrelation of the exemplifying analysis signal illustrated in FIG. 4a, and FIG. 5 shows a schematic illustration of an apparatus according to an exemplifying and non-limiting embodiment of the invention for producing information indicative of cardiac malfunctions.
Figure 5:
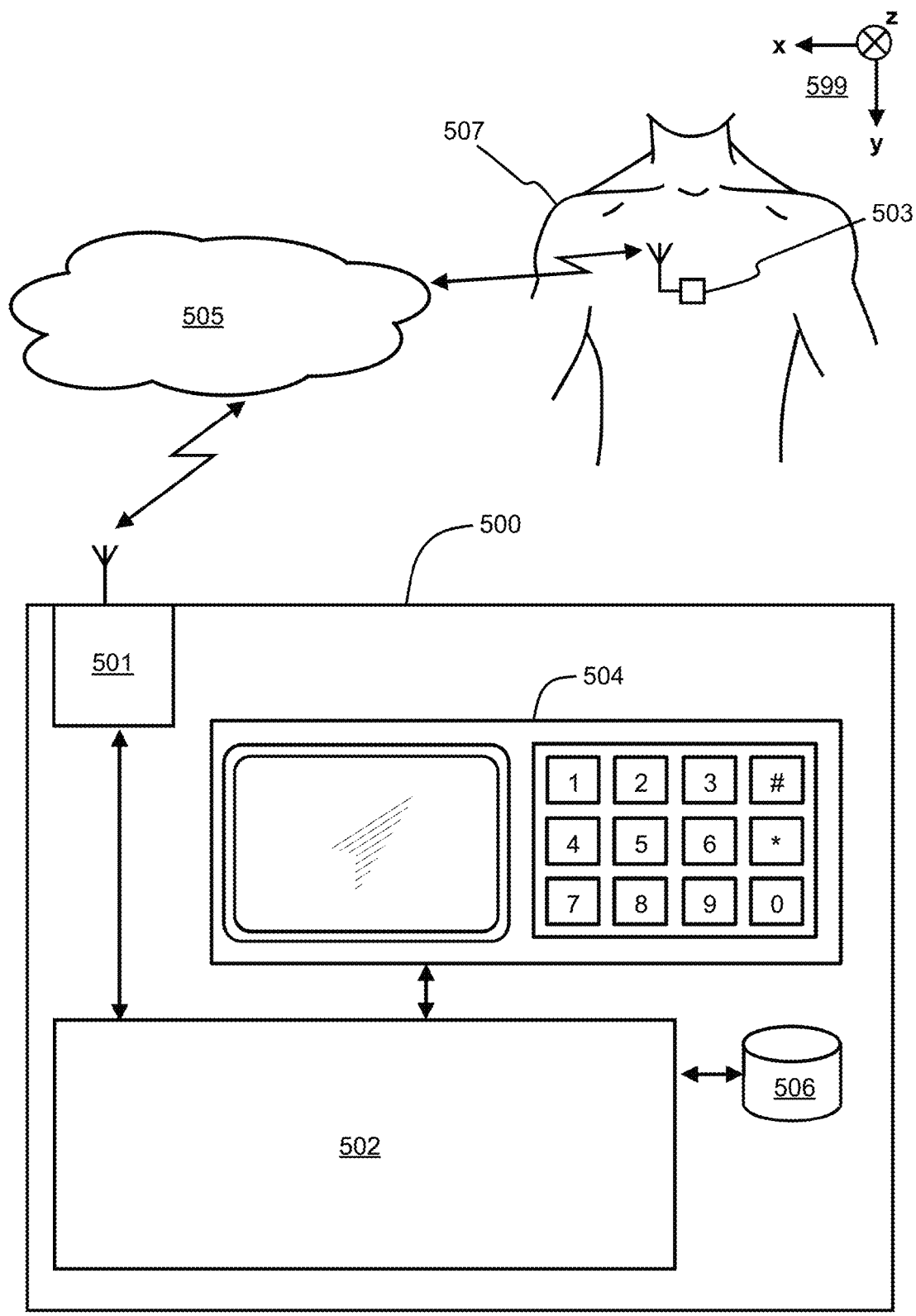

FIG. 3a illustrates an exemplifying waveform of the analysis signal over several heart-beat periods in an exemplifying normal case when an individual under consideration is at rest. FIG. 4a illustrates an exemplifying waveform of the analysis signal over several heart-beat periods in an exemplifying case of atrial fibrillation when an individual under consideration is at rest. The waveforms shown in FIGS. 3a and 4a have been measured with an accelerometer in the "through chest"-direction that is typically referred to as the z-direction. A Cartesian coordinate system 599 shown in FIG. 5 illustrates the z-direction.

Figure 3B:
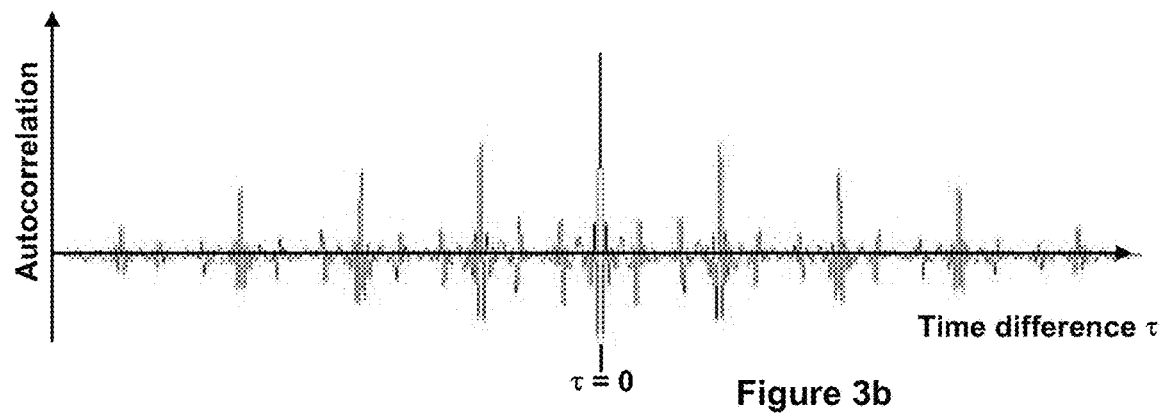
FIG. 3b shows the autocorrelation of the exemplifying analysis signal illustrated in FIG. 3a, FIG. 4a shows a waveform of an exemplifying analysis signal measured with a sensor system responsive to motion in a case of atrial fibrillation when an individual under consideration is at rest.
Figure 4B:
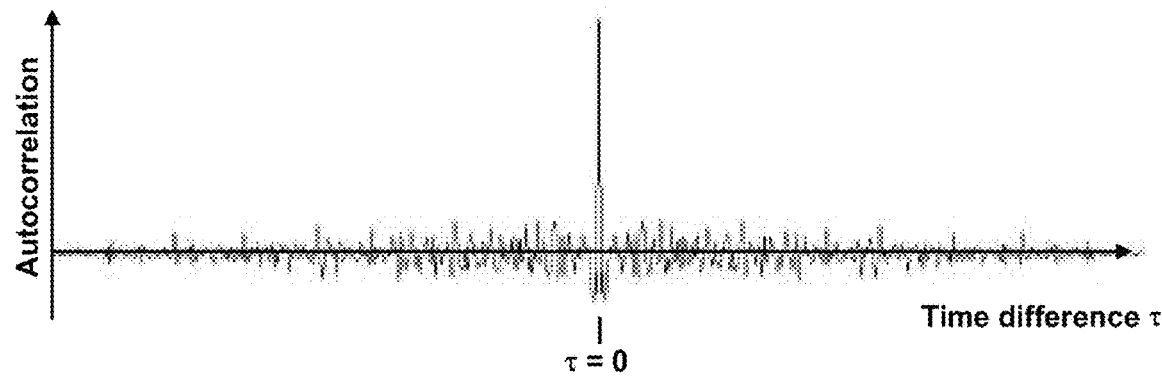

FIG. 3b shows the autocorrelation of the exemplifying analysis signal illustrated in FIG. 3a, and FIG. 4b shows the autocorrelation of the exemplifying analysis signal illustrated in FIG. 4a. In FIGS. 3b and 4b, the time difference is the time difference between analysis signal samples whose mutual correlation is expressed by the autocorrelation. In equation (1) that is presented earlier in this document, $\tau$ represents the time difference. In exemplifying cases where the autocorrelation is defined according to equation (1), the autocorrelation is one at the zero time difference because $R(\tau=0)=E\{(S(t)-\mu)^2\}/\sigma^2=1$.

As can be seen from FIGS. 3b and 4b, the autocorrelation is significantly more concentrated on the point corresponding to the zero time difference, i.e. $\tau=0$, in the case of atrial fibrillation than in the normal case. From FIGS. 3a and 4a it can be seen that the waveform related to the case of atrial fibrillation is more non-periodic than the waveform related to the normal case. Thus, the spectral entropy of the analysis signal is higher in the case of atrial fibrillation than in the normal case.

There are numerous ways to form the above-mentioned first indicator quantity that indicates the degree of concentration of the autocorrelation to the point that corresponds to the zero time difference $\tau=0$. Correspondingly, there are numerous ways to form the above-mentioned second indicator quantity that indicates the spectral entropy of the analysis signal. Exemplifying ways to form the first and second indicator quantities are presented below.

A method according to an exemplifying and non-limiting embodiment of the invention comprises computing an estimate $R_e$ of the autocorrelation of the analysis signal in accordance with the following equation so as to form the first indicator quantity:

$$R_e(\tau) = \text{Average of } \{(S(t)-\mu) \times (S(t-\tau)-\mu)\}/\sigma^2,$$

where the average is computed over time t, S is the analysis signal, $\tau$ is the time difference between two analysis signal samples whose mutual correlation is expressed by $R_e(\tau)$, $\mu$ is the average of the analysis signal, and $\sigma^2$ is the variance of the analysis signal. The first indicator quantity can be formed on the basis of $R_e(\tau=0)$ and a value related to the average of the absolute value of $R_e(\tau)$. The first indicator quantity can be for example:

$$\frac{R_e(\tau=0)}{\text{Average of } \text{abs}(R_e(\tau))}, \text{ or}$$

$$\frac{R_e(\tau=0)}{\text{Average of } (R_e(\tau))^2}, \text{ or}$$

$$\frac{R_e(\tau=0)}{\sqrt{\text{Average of } (R_e(\tau))^2}},$$

where the average is computed over $\tau$, and "abs" means the absolute value.

In many cases, it is also possible to determine heartbeat rates "HR" for successive time periods of the analysis signal on the basis of peaks of autocorrelation estimates computed for the successive time periods of the analysis signal or on the basis of peaks of power spectral density estimates computed for the successive time periods of the analysis signal, and subsequently to determine the heartbeat rate variation "HRV" on the basis of the heartbeat rates "HR" determined for the successive time periods of the analysis signal. Also the heartbeat rate variation "HRV" is a quantity indicative of the irregularity of the waveform of the analysis signal, i.e. indicative of the degree of concentration of the autocorrelation of the analysis signal to the point that corresponds to the zero time difference $\tau=0$. Thus, also the heartbeat rate variation "HRV" or its derivative can be used as the above-mentioned first indicator quantity.

A method according to an exemplifying and non-limiting embodiment of the invention comprises determining temporal lengths of successive heartbeat intervals on the basis of the waveform of the analysis signal, e.g. by searching peaks of the analysis signal. The variation of the temporal lengths of the successive heartbeat intervals is a quantity indicative of the irregularity of the waveform of the analysis signal in the same way as the above-mentioned heartbeat rate variation "HRV" is a quantity indicative of the irregularity of the waveform of the analysis signal. Thus, the variation of the temporal lengths of the successive heartbeat intervals is indicative of the degree of concentration of the autocorrelation of the analysis signal to the point that corresponds to the zero time difference $\tau=0$. Thus, also the variation of the temporal lengths of the successive heartbeat intervals or its derivative can be used as the above-mentioned first indicator quantity.

In many cases it may be, however, challenging to determine the temporal lengths of successive heartbeat intervals on the basis of the waveform of the analysis signal. This is often the case when the quality, e.g. the signal-to-noise ratio "SNR", of the analysis signal is low. In this case, it can be challenging to e.g. detect peaks from the analysis signal in a correct way. The signal quality can be low e.g. when the analysis signal is constituted by a seismocardiography "SCG" signal and/or a gyrocardiography "GCG" signal.

In a method according to an exemplifying and non-limiting embodiment of the invention, the analysis signal comprises two or more simultaneously measured signal components so that the signal components correspond to different measurement directions. For example, the analysis signal may comprise six signal components S1, S2, S3, S4, S5, and S6 so that:

S1 is linear acceleration measured in the x-direction,
S2 is linear acceleration measured in the y-direction,
S3 is linear acceleration measured in the z-direction,
S4 is measured rotational, i.e. gyroscopic, acceleration around the x-axis,
S5 is measured rotational acceleration around the y-axis, and
S6 is measured rotational acceleration around the z-axis.

The coordinate system 599 shown in FIG. 5 illustrates the x, y, and z-directions.

In this exemplifying case, the sensor system for measuring the analysis signal may comprise a single six-axis sensor or the sensor system may comprise three accelerometers and three gyroscopes. In the method according to this exemplifying and non-limiting embodiment of the invention, an estimate for the temporal length of each heartbeat interval is formed by choosing, from among candidate temporal lengths indicated by the two or more signal components, a particular candidate temporal length which is closest to the temporal length of the previous heartbeat period so that the absolute value of the difference between the chosen candidate temporal length and the temporal length of the previous heartbeat interval is as small as possible. For example, if the temporal length of a heartbeat period n is T(n) and if, from among candidate temporal lengths T1(n+1), T2(n+1), ..., Tk(n+1), ... indicated by the signal components S1, S2, ... Sk, ... for the heartbeat period n+1, the candidate temporal length Tk(n+1) is closest to the temporal length T(n), then the temporal length of the heartbeat period n+1 is chosen to be the candidate temporal length Tk(n+1). This method for determining the temporal lengths of heartbeat periods is based on that a rapid change in the temporal length when successive heartbeat periods are concerned refers to an error in the determination of the temporal lengths.

A method according to an exemplifying and non-limiting embodiment of the invention comprises computing an estimate $SE_e$ of the spectral entropy of the analysis signal in accordance with the following equation so as to form the second indicator quantity:

$$SE_e = \text{Average of } \{-PSD_n(f)\log_2[PSD_n(f)]\},$$

where $PSD_n(f)$ is the normalized power spectral density that is the power spectral density of the analysis signal divided by the power of the analysis signal and f is the frequency. The average is computed over the frequency f from $-f_s/2$ to $f_s/2$, where $f_s$ is the sample rate. The computed estimate $SE_e$, or its suitable derivative, can be used as the second indicator quantity.

A method according to an exemplifying and non-limiting embodiment of the invention comprises optionally measuring the analysis signal with a sensor element from an individual's body. A method according to another exemplifying and non-limiting embodiment of the invention comprises reading the analysis signal from a memory, in which case the analysis signal has been measured earlier and recorded to the memory. A method according to an exemplifying and non-limiting embodiment of the invention comprises receiving the analysis signal from an external data transfer system. Therefore, the measuring is not an essential and necessary step of methods according to many embodiments of the invention but the analysis signal, or the output signal of the sensor system, is to be understood as an input quantity of the methods.

A computer program according to an exemplifying and non-limiting embodiment of the invention comprises computer executable instructions for controlling a programmable processing system to carry out actions related to a method according to any of the above-described exemplifying embodiments of the invention.

A computer program according to an exemplifying and non-limiting embodiment of the invention comprises software modules for producing information indicative of cardiac malfunctions, e.g. atrial fibrillation, on the basis of the above-mentioned analysis signal. The software modules comprise computer executable instructions for controlling a programmable processing system to:

form a first indicator quantity indicating degree of concentration of the autocorrelation of the analysis signal to a point that corresponds to the zero time difference between analysis signal samples whose mutual correlation is expressed by the autocorrelation form a second indicator quantity indicating the spectral entropy of the analysis signal, and determine an indicator of cardiac malfunction on the basis of at least the first indicator quantity and the second indicator quantity.

The software modules can be e.g. subroutines or functions implemented with a suitable programming language and with a compiler suitable for the programming language and for the programmable processing system under consideration. It is worth noting that also a source code corresponding to a suitable programming language represents the computer executable software modules because the source code contains the information needed for controlling the programmable processing system to carry out the above-presented actions and compiling changes only the format of the information. Furthermore, it is also possible that the programmable processing system is provided with an interpreter so that a source code implemented with a suitable programming language does not need to be compiled prior to running.

A computer program product according to an exemplifying and non-limiting embodiment of the invention comprises a computer readable medium, e.g. a compact disc ("CD"), encoded with a computer program according to an embodiment of invention.

A signal according to an exemplifying and non-limiting embodiment of the invention is encoded to carry information defining a computer program according to an embodiment of invention.

FIG. 5 illustrates a schematic illustration of an apparatus 500 according to an exemplifying and non-limiting embodiment of the invention for producing information indicative of cardiac malfunctions, e.g. atrial fibrillation. The apparatus comprises a processing system 502 for processing an analysis signal produced by a sensor system responsive to motion including cardiovascular motion. The processing system 502 is configured to:

form a first indicator quantity indicating degree of concentration of the autocorrelation of the analysis signal to a point that corresponds to the zero time difference between analysis signal samples whose mutual correlation is expressed by the autocorrelation, form a second indicator quantity indicating the spectral entropy of the analysis signal, and determine an indicator of cardiac malfunction on the basis of at least the first indicator quantity and the second indicator quantity.

In the exemplifying case illustrated in FIG. 5, the apparatus comprises a radio receiver 501 for receiving the analysis signal from a data transfer network 505. The analysis signal is produced by a sensor element 503 that comprises the above-mentioned sensor system for measuring the analysis signal and a radio transmitter for transmitting the analysis signal to the data transfer network 505. The data transfer network 505 can be for example a telecommunications network. It is also possible that there is a direct radio link or a direct corded link from the sensor element 503 to the apparatus 500. Furthermore, it is also possible that there is a radio link or a corded link directly or via the data transfer network 505 from the apparatus 500 to the sensor element 503 so as to enable the apparatus to control the operation of the sensor element 503. It is also possible that the whole apparatus is integrated into the sensor element 503.

In an apparatus according to an exemplifying and non-limiting embodiment of the invention, the processing system 502 is configured to detect, from an output signal of the sensor system, periods when an individual 507 being measured is at rest and to extract the analysis signal from the output signal of the sensor system so that the analysis signal corresponds to a situation where the individual 507 is at rest. It is also possible that the sensor element 503 comprises a processor for detecting whether the individual 507 is at rest and for extracting the analysis signal from the output signal of the sensor system.

The sensor system for producing the analysis signal may comprises for example an accelerometer, a gyroscope, and/or an inertial measurement unit "IMU" comprising both an accelerometer and a gyroscope. In addition to the sensor system, the sensor element 503 may further comprise for example an amplifier, a signal filter, an analog-to-digital "AD" converter, and/or the above-mentioned processor for detecting whether the individual 507 is at rest. An accelerometer can be for example a three-axis accelerometer which is capable of measuring movements independently in three mutually orthogonal directions x, y, and z of e.g. the coordinate system 599 shown in FIG. 5. In this exemplifying case, the analysis signal can be for example the Euclidian norm, i.e. the absolute value, of the vector representing the movements measured in the three mutually orthogonal directions.

In an apparatus according to an exemplifying and non-limiting embodiment of the invention, the processing system 502 is configured to determine temporal lengths of successive heartbeat intervals on the basis of the waveform of the analysis signal, e.g. by searching peaks of the analysis signal. The variation of the temporal lengths of the successive heartbeat intervals is a quantity indicative of the irregularity of the waveform of the analysis signal. Thus, the variation of the temporal lengths of the successive heartbeat intervals is indicative of the degree of concentration of the autocorrelation of the analysis signal to the point that corresponds to the zero time difference $\tau=0$. Thus, the variation of the temporal lengths of the successive heartbeat intervals or its derivative can be used as the above-mentioned first indicator quantity.

In an apparatus according to an exemplifying and non-limiting embodiment of the invention, the analysis signal which is produced by the sensor system comprises two or more signal components so that the signal components correspond to different measurement directions. For example, the analysis signal may comprise six signal components S1, S2, S3, S4, S5, and S6 so that:

S1 is linear acceleration measured in the x-direction,
S2 is linear acceleration measured in the y-direction,
S3 is linear acceleration measured in the z-direction,
S4 is measured rotational, i.e. gyroscopic, acceleration around the x-axis,
S5 is measured rotational acceleration around the y-axis, and
S6 is measured rotational acceleration around the z-axis.

The coordinate system 599 shown in FIG. 5 illustrates the x, y, and z-directions.

In this exemplifying case, the sensor system may comprise a single six-axis sensor or the sensor system may comprise three accelerometers and three gyroscopes.

In an apparatus according to an exemplifying and non-limiting embodiment of the invention, the processing system 502 is configured to form an estimate for the temporal length of each heartbeat interval by choosing, from among candidate temporal lengths indicated by the two or more signal components, a particular candidate temporal length which is closest to the temporal length of the previous heartbeat period so that the absolute value of the difference between the chosen candidate temporal length and the temporal length of the previous heartbeat interval is as small as possible.

In an apparatus according to an exemplifying and non-limiting embodiment of the invention, the processing system 502 is configured to:

determine the first and second indicator quantities for each of two or more analysis signals being mutually different temporal portions of the output signal of the sensor system and being advantageously measured when the individual 507 is at rest, and determine the indicator of cardiac malfunction on the basis of the first and second indicator quantities determined for the two or more analysis signals.

In an apparatus according to an exemplifying and non-limiting embodiment of the invention, the processing system 502 is configured to receive at least one of the above-mentioned analysis signals from an accelerometer of the sensor system and at least one other of the analysis signals from a gyroscope of the sensor system.

In an apparatus according to an exemplifying and non-limiting embodiment of the invention, the processing system 502 is configured to compute an estimate $R_e$ of the autocorrelation of the analysis signal in accordance with the following equation:

$$R_e(T) = \text{Average of } \{(S(t)-\mu) \times (S(t-\tau)-\mu)\}/\sigma^2,$$

where the average is computed over time t, S is the analysis signal, $\tau$ is the time difference between analysis signal samples whose mutual correlation is expressed by $R_e(\tau)$, $\mu$ is the average of the analysis signal, and $\sigma^2$ is the variance of the analysis signal. The first indicator quantity indicating the degree of concentration of the autocorrelation can be formed on the basis of $R_e(\tau=0)$ and a value related to the average of the absolute value of $R_e(\tau)$.

In an apparatus according to an exemplifying and non-limiting embodiment of the invention, the processing system 502 is configured to determine heartbeat rates "HR" for successive time periods of the analysis signal on the basis of peaks of autocorrelation estimates computed for the successive time periods of the analysis signal or on the basis of peaks of power spectral density estimates computed for the successive time periods of the analysis signal, and subsequently to determine the heartbeat rate variation "HRV" on the basis of the heartbeat rates "HR" determined for the successive time periods of the analysis signal. The heartbeat rate variation "HRV" or its derivative can be used as the above-mentioned first indicator quantity.

In an apparatus according to an exemplifying and non-limiting embodiment of the invention, the processing system 502 is configured to form an estimate $SE_e$ of the spectral entropy of the analysis signal in accordance with the following equation:

$$SE_e = \text{Average of } \{-PSD_n(f) \log_2 [PSD_n(f)]\}$$

where $PSD_n(f)$ is the normalized power spectral density and the average is computed over the frequency f from $-f_s/2$ to $f_s/2$, $f_s$ being the sample rate. The second indicator quantity can be the computed estimate $SE_e$ or its suitable derivative.

In an apparatus according to an exemplifying and non-limiting embodiment of the invention, the processing system 502 is configured to set the indicator of cardiac malfunction to indicate a situation in which the first indicator quantity exceeds a first threshold value and the second indicator quantity exceeds a second threshold value. The cardiac malfunction, e.g. atrial fibrillation, can be deemed to be present when the first indicator quantity exceeds the first threshold value and the second indicator quantity exceeds the second threshold value.

An apparatus according to an exemplifying embodiment of the invention comprises means for pre-processing the analysis signal prior to forming the above-mentioned first and second indicator quantities. The pre-processing may comprise, for example, cancellation of noise caused by e.g. breathing, tremble caused by external reasons, etc. The means for the pre-processing can be, for example, implemented with the processing system 502 or there can be one or more separate processing devices for the pre-processing.

An apparatus according to an exemplifying and non-limiting embodiment of the invention is configured to record the signal received from the sensor element 503. The apparatus may comprise an internal memory 506 for recording the signal or the apparatus may comprise a data port for connecting to an external memory. The apparatus may further comprise a user interface 504 or a data port for connecting to an external user interface device.

In an apparatus according to an exemplifying and non-limiting embodiment of the invention, the processing system 502 is configured to run a machine learning algorithm for training the processing system 502 to determine the indicator of cardiac malfunction on the basis of at least information contained by the analysis signal.

The machine learning algorithm can be based on supervised machine learning or unsupervised machine learning. In the supervised machine learning, the processing system is supplied with training data and the known classification of the training data. Thus, the processing system 502 is enabled to learn what kind of data is classified in a certain way. For example, a first numerical range of the first indicator quantity and a first numerical range of the second indicator quantity may correspond to the class of the indicator of cardiac malfunction: "No malfunction, healthy", a second numerical range of the first indicator quantity and the first numerical range of the second indicator quantity may correspond to the class of the indicator of cardiac malfunction: "malfunction probability 30%", etc. In the unsupervised machine learning, the processing system is supplied with data without classification information and the processing system classifies the supplied data on the basis of properties of the supplied data. Thereafter, a human can recognize different classes from the machine classified data. In some cases, the unsupervised machine learning can be used for generating a starting point for supervised machine learning.

It is also possible that the machine learning algorithm trains the processing system 502 to determine the indicator of cardiac malfunction directly on the basis of the signal properties of the analysis signal. In this case, the first indicator quantity indicating the degree of concentration of the autocorrelation of the analysis signal and the second indicator quantity indicating the spectral entropy of the analysis signal are internal quantities of the machine learning algorithm. The signal properties of the analysis signal may comprise for example features describing: the degree of periodicity, the frequency spectrum, statistical parameters such as average, variance, moments, etc. and/or other features describing the analysis signal. Features of the kind mentioned above can be obtained with e.g. the wavelet transform, the Fourier transform, and/or the Fast Fourier transform. Other features can be for example the turning-point ratio, the heartbeat rate, the heartbeat rate variation, etc. It is also possible to remove noise from the analysis signal with the aid of the machine learning and/or with a suitable pre-processing carried out prior to the machine learning.

The vector of features, i.e. a feature vector, extracted from the analysis signal and used in the supervised or unsupervised machine learning can be reduced by using suitable methods such as for example the Principal Component Analysis "PCA" and the Independent Component Analysis "ICA". The reduction of the feature vector may speed up the supervised or unsupervised machine learning and/or improve the accuracy of the machine learning.

The feature vector can be formed for example on the basis of signal components related to e.g. seismocardiography "SCG" and/or gyrocardiography "GCG" and measured simultaneously in different measurement directions. For example, samples of linear acceleration in the x-direction can constitute a partial feature vector F1, samples of linear acceleration in the y-direction can constitute a partial feature vector F2, samples of linear acceleration in the z-direction can constitute a partial feature vector F3, samples of rotational acceleration around the x-axis can constitute a partial feature vector F4, samples of rotational acceleration around the y-axis can constitute a partial feature vector F5, and samples of rotational acceleration around the z-axis can constitute a partial feature vector F6. The feature vector F that is supplied to the machine learning algorithm can be formed e.g. as a concatenation of the partial feature vectors F1-F6, i.e. F=[F1, F2, F3, F4, F5, F6] where the partial feature vectors F1-F6 are row vectors. This enables the machine learning algorithm to combine and utilize information related to the different measurement directions and measurement modes—linear, rotational.

It is also possible to utilize the information related to the different measurement directions in other ways too. For example, the partial feature vectors F1-F6 can be arranged to constitute a matrix having dimensions NS×6 or 6×NS, where NS is the number of samples in each of the partial feature vectors F1-F6, i.e. the length of each partial feature vector. This matrix can be processed with one or more feature extraction algorithms designed for two or more dimensional cases.

The processing system 502 can be implemented with one or more processor circuits, each of which can be a programmable processor circuit provided with appropriate software, a dedicated hardware processor such as for example an application specific integrated circuit "ASIC", or a configurable hardware processor such as for example a field programmable gate array "FPGA".

Nowadays many mobile communication devices, e.g. mobile phones, comprise sensors such as an accelerometer and/or a gyroscope. Thus, a mobile communication device, e.g. a mobile phone, of the kind mentioned above can be used as the sensor element responsive to motion including cardiovascular motion. It is also possible that the whole apparatus is included into a mobile communication device, e.g. a mobile phone.

The specific examples provided in the description given above should not be construed as limiting the scope and/or the applicability of the appended claims. Lists and groups of examples provided in the description given above are not exhaustive unless otherwise explicitly stated.

What is claimed is:

1. An apparatus comprising:
    a sensor system responsive to motion including cardiovascular motion, the sensor system comprising at least one of the following: an accelerometer, a gyroscope, an inertial measurement unit comprising both an accelerometer and a gyroscope,
    a processing system for processing an analysis signal produced by the sensor system,
    wherein the processing system is configured to:
        form a first indicator quantity indicating degree of concentration of autocorrelation of the analysis signal to a point that corresponds to zero time difference between analysis signal samples whose mutual correlation is expressed by the autocorrelation,
        form a second indicator quantity indicating spectral entropy of the analysis signal, and
        determine an indicator of cardiac malfunction on the basis of at least the first indicator quantity and the second indicator quantity.

2. An apparatus according to claim 1, wherein the processing system is configured to detect, from an output signal of the sensor system, a period when an individual measured with the sensor system is at rest and to extract the analysis signal from the output signal of the sensor system so that the analysis signal corresponds to a situation where the individual is at rest.

3. An apparatus according to claim 2, wherein the processing system is configured to:
    determine the first and second indicator quantities for each of two or more analysis signals being mutually different temporal portions of an output signal of the sensor system, and
    determine the indicator of cardiac malfunction on the basis the first and second indicator quantities determined for the two or more analysis signals.

4. An apparatus according to claim 3, wherein the processing system is configured to receive at least one of the analysis signals from an accelerometer of the sensor system and at least one other of the analysis signals from a gyroscope of the sensor system.

5. An apparatus according to claim 1, wherein the processing system is configured to:
    determine the first and second indicator quantities for each of two or more analysis signals being mutually different temporal portions of an output signal of the sensor system, and determine the indicator of cardiac malfunction on the basis the first and second indicator quantities determined for the two or more analysis signals.

6. An apparatus according to claim 5, wherein the processing system is configured to receive at least one of the analysis signals from an accelerometer of the sensor system and at least one other of the analysis signals from a gyroscope of the sensor system.

7. An apparatus according to claim 1, wherein the processing system is configured to compute an estimate $R_e$ of the autocorrelation of the analysis signal in accordance with the following equation:

$$R_e(\tau) = \text{Average of } \{(S(t)-\mu) \times (S(t-\tau)-\mu)\}/\sigma^2,$$

where the average is computed over time t, S is the analysis signal, $\tau$ is a time difference between analysis signal samples whose mutual correlation is expressed by $R_e(\tau)$, $\mu$ is an average of the analysis signal, and $\sigma^2$ is a variance of the analysis signal.

8. An apparatus according to claim 7, wherein the processing system is configured to form the first indicator quantity on the basis of $R_e(\tau=0)$ and a value related to an average of an absolute value of $R_e(\tau)$.

9. An apparatus according to claim 1, wherein the processing system is configured to form an estimate $SE_e$ of the spectral entropy of the analysis signal in accordance with the following equation so as to form the second indicator quantity:

$$SE_e = \text{Average of } \{-PSD_n(f) \log_2 [PSD_n(f)]\}$$

where the average is computed over frequency f from $-f_s/2$ to $f_s/2$, $f_s$ is a sample rate, and $PSD_n(f)$ is a normalized power spectral density being a power spectral density of the analysis signal divided by power of the analysis signal.

10. An apparatus according to claim 1, wherein the processing system is configured to compare the first indicator quantity to a first threshold value and compare the second indicator quantity to a second threshold value so as to determine the indicator of cardiac malfunction.

11. An apparatus according to claim 1, wherein the processing system is configured to determine heartbeat rates for successive time periods of the analysis signal on the basis of peaks of autocorrelation estimates computed for the successive time periods of the analysis signal, to determine heartbeat rate variation on the basis of the heartbeat rates determined for the successive time periods of the analysis signal, and to form the first indicator quantity based on the determined heartbeat rate variation.

12. An apparatus according to claim 1, wherein the processing system is configured to determine temporal lengths of successive heartbeat intervals on the basis of a waveform of the analysis signal and to compute a variation of the temporal lengths of the successive heartbeat intervals so as to form the first indicator quantity.

13. An apparatus according to claim 12, wherein the processing system is configured to form an estimate for the temporal length of each heartbeat interval by choosing, from among candidate temporal lengths indicated by two or more signal components of the analysis signal, a particular one of the candidate temporal lengths which is closest to the temporal length of a previous heartbeat period so that an absolute value of a difference between the chosen candidate temporal length and the temporal length of the previous heartbeat interval is as small as possible, the signal components of the analysis signal corresponding to different measurement directions of the motion including the cardiovascular motion.

14. An apparatus according to claim 13, wherein the apparatus comprises the sensor system and the sensor system is suitable for measuring the signal components S1, S2, S3, S4, S5, and S6 of the analysis signal where:
   S1 is linear acceleration measured in an x-direction,
   S2 is linear acceleration measured in a y-direction,
   S3 is linear acceleration measured in a z-direction,
   S4 is measured rotational acceleration around an x-axis,
   S5 is measured rotational acceleration around a y-axis, and
   S6 is measured rotational acceleration around a z-axis,
      where the x-, y-, and z-axes are axes of a Cartesian coordinate system and the x-, y-, and z-directions are directions of the x-, y-, and z-axes.

15. An apparatus according to claim 1, wherein the processing system is configured to run a machine learning algorithm for training the processing system to determine the indicator of cardiac malfunction on the basis of at least information contained by the analysis signal.

16. An apparatus according to claim 1, wherein the indicator of cardiac malfunction is an indicator of atrial fibrillation.

17. A method comprising:
   forming (201) a first indicator quantity indicating degree of concentration of autocorrelation of an analysis signal to a point that corresponds to zero time difference between analysis signal samples whose mutual correlation is expressed by the autocorrelation,
   forming (202) a second indicator quantity indicating spectral entropy of the analysis signal, and
   determining (203) an indicator of cardiac malfunction on the basis of at least the first indicator quantity and the second indicator quantity,
wherein the analysis signal is a signal produced by a sensor system responsive to motion including cardiovascular motion, the sensor system comprising at least one of the following: an accelerometer, a gyroscope, an inertial measurement unit comprising both an accelerometer and a gyroscope.

* * * * *